United States Patent
Cramer et al.

(10) Patent No.: US 7,073,369 B2
(45) Date of Patent: Jul. 11, 2006

(54) METHOD AND DEVICE FOR DETECTING THE CONCENTRATION OF AN OXYGEN-CONTAINING COMPOUND IN AN ANALYTE GAS

(75) Inventors: Berndt Cramer, Leonberg (DE); Bernd Schumann, Rutesheim (DE)

(73) Assignee: Robert Bosch GmbH, Stuttgart (DE)

( * ) Notice: Subject to any disclaimer, the term of this patent is extended or adjusted under 35 U.S.C. 154(b) by 42 days.

(21) Appl. No.: 10/473,357

(22) PCT Filed: Feb. 27, 2002

(86) PCT No.: PCT/DE02/00724

§ 371 (c)(1),
(2), (4) Date: Sep. 30, 2003

(87) PCT Pub. No.: WO02/079769

PCT Pub. Date: Oct. 10, 2002

(65) Prior Publication Data

US 2004/0089055 A1    May 13, 2004

(30) Foreign Application Priority Data

Mar. 31, 2001   (DE) ................................ 101 16 184

(51) Int. Cl.
*G01N 7/00*       (2006.01)
*G01N 27/25*    (2006.01)
(52) U.S. Cl. ...................................... 73/23.31; 204/424
(58) Field of Classification Search ............... 73/23.31; 204/424
See application file for complete search history.

(56) References Cited

U.S. PATENT DOCUMENTS 5,763,763 A  *  6/1998 Kato et al. ................... 73/23.2
5,879,525 A  *  3/1999 Kato ........................... 204/424

(Continued)

FOREIGN PATENT DOCUMENTS

EP        0392447       10/1990

(Continued)

OTHER PUBLICATIONS

"Thick Film ZrO2 NOx Sensor" by Kato et al, SAE Technical Paper Series 960334, International Congress & Exposition, Detroit, Michigan, 1996, pp. 137 to 142.

*Primary Examiner*—Hezron Williams
*Assistant Examiner*—John Fitzgerald
(74) *Attorney, Agent, or Firm*—Walter Ottesen

(57) ABSTRACT

A method and an arrangement for determining the concentration of an oxygen-containing compound in a test gas in an external volume are presented with the external volume containing also additional oxygen. The method utilizes a sensor having a first cavity which is connected to the external volume via a first diffusion barrier and a second cavity which is connected to the first cavity via a further diffusion barrier. In addition, means for reducing the oxygen concentration in the first cavity and means for detecting the concentration of oxygen in the second cavity are provided. The reduction of the oxygen concentration in the first cavity takes place in a first phase to a value at which a change of the concentration of the oxygen-containing compound does not occur. In a second phase, a further reduction takes place in the first chamber to a value at which also a reduction of the concentration of the first oxygen-containing compound occurs. An index for the sought-after concentration is formed as the difference of the oxygen concentrations detected in the first and second phases in the second cavity.

6 Claims, 3 Drawing Sheets

U.S. PATENT DOCUMENTS 6,010,615 A * 1/2000 Kato et al. ............... 205/784.5
6,071,393 A * 6/2000 Oshima et al. ............. 204/425
6,635,162 B1 * 10/2003 Sugaya et al. .............. 204/426

FOREIGN PATENT DOCUMENTS

EP         0678740      10/1995
WO     WO 99 57556     11/1999

* cited by examiner

METHOD AND DEVICE FOR DETECTING THE CONCENTRATION OF AN OXYGEN-CONTAINING COMPOUND IN AN ANALYTE GAS

RELATED APPLICATION

This application is the national stage of PCT/DE 02/00724, filed Feb. 27, 2002, designating the United States and claiming priority from German patent application 101 16 184.0 filed Mar. 31, 2001.

1. Field of the Invention

The invention relates to the detection of the concentration of a specific oxygen-containing compound in a test gas which contains still further oxygen-containing compounds.

As a test gas, especially the exhaust gas of an internal combustion engine is of interest. The specific oxygen-containing compound, whose concentration is to be detected, can be nitrogen oxide. Other oxygen-containing compounds of interest are especially molecular oxygen, carbon monoxide, carbon dioxide and water.

2. Background of the Invention

An NOx sensor having two cavities is known from SAE Paper 960334 and from European patent publication 0,678,740. These two cavities are delimited by an ion-conducting solid electrolyte. The first cavity communicates with the test gas via a first diffusion boundary. The first and second cavities are connected to each other via a further diffusion boundary. The concentration of oxygen in the first cavity is reduced to a predetermined value by a first electrolytic oxygen pumping cell.

For this purpose, a pump voltage is so applied to the electrolyte via electrodes that the resulting electric field in the electrolyte drives a flow of oxygen ions from the cavity. By appropriately selecting the physical conditions such as: the temperature, the selectively catalytic effect of the electrolyte material and the pump voltage, it can be achieved that the specific oxygen-containing compound (for example, NOx), the concentration of which is to be detected, makes no contribution to the oxygen pump current from the first cavity. If, for example, nitrogen oxides define the specific oxygen-containing compound, the above-mentioned physical conditions can be so pregiven that a decomposition into nitrogen and oxygen does not occur at the electrode of the first cavity. Oxygen from this compound can then not be pumped away and therefore can provide no contribution to the oxygen pump current of the first cavity.

In the second cavity, a second electrolytic pump cell reduces the oxygen concentration further. With decreasing oxygen concentration, this has the consequence of a separation of the nitrogen oxides into oxygen and nitrogen. The intensity of the pump flow in the second cavity is used as an index for the NOx concentration in the test gas. The principle of this sensor is based on the fact that the pumping off of oxygen from the second cavity disturbs the equilibrium of the reactions NOx<-->1/2N2+1/2O2 and favors the right side of the equation.

NO is decomposed in the second cavity with an oxygen pump operation. For this reason, the NOx compounds feed the pump flow of the second cavity. Furthermore, because the O2 concentration is assumed as known and constant due to the upstream connected first pump cell, the NOx quantity in the test gas can be determined from the intensity of the pump current from the second cavity.

Sensors of the state of the art exhibit an offset, a drift and an intense temperature dependency of the pump current. These disadvantages are based on the following causes.

Offset quantities arise in the nitrogen oxide measurement signal even in the absence of nitrogen oxides because of the electronic residual conductivity of oxygen conductive solid electrolytes as well as because of Seebeck voltages and electric field coupling and current coupling. Because of structural changes during the operation, the electric characteristics of the solid electrolyte change in such a manner that a drift occurs in the signal amplitude as well as in the signal zero position.

SUMMARY OF THE INVENTION

In view of this background, it is the task of the invention to minimize the offset, the deterioration drift and the temperature dependency of the signal for the sought-after concentration of the specific oxygen-containing compound.

In detail, a first sensor having a first cavity is used in a method for determining the concentration of an oxygen-containing compound in a test gas in an external volume which also contains additional oxygen. The first cavity is connected to the external volume via a first diffusion barrier and the first cavity is connected to a second cavity via an additional diffusion barrier.

Furthermore, means are provided for reducing the oxygen concentration in the first cavity and means are provided for detecting the concentration of oxygen in the second cavity. According to the invention, the reduction of the oxygen content takes place in the first cavity in a first phase to a value at which a change of the concentration of the oxygen-containing compound does not occur and, in addition, in a second phase, a further reduction in the first cavity takes place to a value at which a reduction of the concentration of the first oxygen-containing compound also occurs. The above-mentioned index for the sought concentration is formed as the difference of the oxygen concentrations detected in the first phase and in the second phase in the second cavity.

In contrast to the evaluation methods, which are known from the state of the art, and for which the voltage of the pump electrode of the first cavity is controlled to a fixed value relative to the air reference electrode, a reversal according to the invention takes place alternately between two values $U_{IPE\_H}$, $U_{IPE\_L}$.

The pump current of the second chamber is recorded at $U_{IPE\_H}$ as well as at $U_{IPE\_L}$. As an index for the sought concentration of the specific oxygen-containing compound, the difference of the pump currents of the second cavity is formed at $U_{IPE\_H}$ and $U_{IPE\_L}$.

The formation of the difference of the values of the pump current from the second cavity effects the sought-after minimization of the offset, the deterioration drift and the temperature dependency with these values of the pump current being recorded at two different pump voltages. The difference formation effects a zero equalization of the pump current of the second cavity to a certain extent. Stated otherwise, the method of the invention can also be characterized as a pendular operation of the first oxygen pump electrode with respect to the pump voltage. The pendular operation according to the invention makes possible the offset measurement and low drift measurement because of a continuous zero equalization.

In this way, the following advantages are obtained.

Temperature changes in the sensor operate similarly on signal magnitude and zero position so that a reduction of the temperature coefficient of the nitrogen oxide signal is achieved via the pendular method.

For the signal errors, which result from the current coupling and field coupling, the improvement is still greater because the errors occur almost identically with respect to signal magnitude and zero position.

With the continuous determination of the zero position, the drift of the zero position becomes insignificant.

Pulse-shaped disturbances, which, for example, result from high-frequency interferences, can be greatly reduced utilizing a validity test of the measured values.

BRIEF DESCRIPTION OF THE DRAWING

The invention will now be described with reference to the drawings wherein.

DECSRIPTION OF THE PREFERRED EMBODIMENTS OF THE INVENTION

Figure 1:
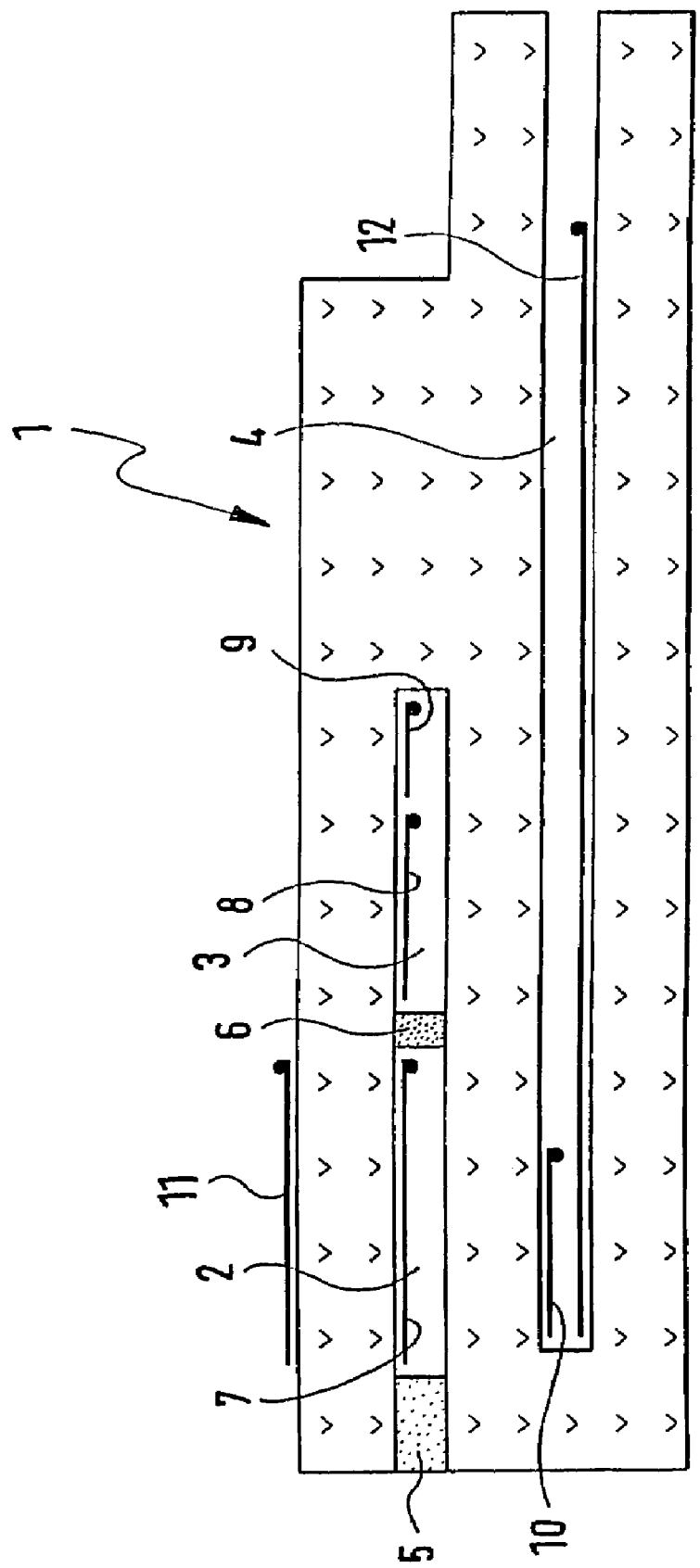
FIG. 1 shows a double-cavity NOx sensor as is suitable for carrying out the method of the invention.

Reference numeral 1 in FIG. 1 identifies a solid electrolyte having three cavities 2, 3 and 4 as well as diffusion barriers 5 and 6 and electrodes 7 to 11 and a heater 12.

The first cavity 2 is connected via the diffusion barrier 5 to the exhaust gas and via the second diffusion barrier 6 to the second cavity 3. The first cavity or the second cavity can, in turn, comprise several cavities. The third cavity 4 is connected via a channel only to the air and contains the air reference electrode 10.

The oxygen pump electrode 7 functions as a negative electrode of the oxygen pump of the first cavity.

The electrode 8 functions as a negative electrode of the oxygen pump of the second cavity. As described above, the pump current can, under specific conditions, function as an index for the sought concentration of the nitrogen oxides or another oxygen-containing compound.

In addition to the electrode 8, a further pump electrode 9 can be provided in the second cavity and the material of this pump electrode can facilitate, for example, the decomposition of nitrogen oxides.

An electrode, which is more positive in the direct comparison, functions in each case as a positive counter electrode for the oxygen pump operation. This can, for example, be the external pump electrode 11.

The pump current of the nitrogen can be measured at the pump electrode 9.

The pump electrode 9 has the most negative potential. For this reason, all other electrodes are appropriate as counterelectrodes for this electrode. Depending upon the field geometry in the solid electrolyte, these counterelectrodes can also be several of the other more positive electrodes.

An isolated heater 12 brings the sensor to the needed operating temperature.

The sensor shown makes possible the following functions.

Test gas arrives in the first cavity 2 via the first diffusion barrier 5. The test gas contains at least one oxygen-containing component in addition to molecular oxygen with the oxygen-containing component having a concentration in the test gas which is to be determined. Nitrogen oxides define one example of such an oxygen-containing component.

An electrode 7 forms an oxygen pump in combination with a positive electrode and the ion-conducting solid electrolyte lying between the two electrodes. Electrode 8 forms an oxygen pump in combination with a positive electrode and the ion-conducting solid electrode lying between the two electrodes. Electrode 9 forms an oxygen pump in combination with a positive electrode and the ion-conducting solid electrode lying in between these two electrodes. Especially the electrode 11 is appropriate as a positive counterelectrode.

A potential difference between the electrodes generates an electric field in the electrolyte which drives the oxygen ion pump current.

With the selection of a suitable electrode material, for example, the dissociation of oxygen molecules can be preferred relative to the separation of other oxygen-containing compounds.

If, for example, the concentration of nitrogen oxides is to be detected, then it is advantageous when the oxygen pump electrode 7 facilitates the dissociation of oxygen but not of nitrogen oxide.

In contrast, the NO pump electrode 9 should, in this case, have a nitrogen oxide decomposing action.

The oxygen pump of the first cavity reduces the oxygen content of the test gas in the first cavity by pumping off oxygen ions which originate from molecular oxygen but not from the at least one oxygen-containing component.

In sensors of the state of the art, the potential of the external pump electrode is controlled to a fixed value relative to the air reference electrode. The greater the potential difference, the lower is the oxygen concentration which adjusts in the first cavity. The fixed value is so predetermined for the sensor in the state of the art that the oxygen content, which remains in the first cavity, cannot go to zero. In this way, a decomposition of nitrogen oxides in the first cavity is avoided.

In contrast, the invention utilizes at least two potential values for the external pump electrode between which there is a reversal during operation of the sensor.

The test gas with reduced oxygen content reaches the second cavity via a second diffusion barrier. There, additional oxygen is pumped away so that, for a decreasing oxygen content in the second cavity, also the at least one oxygen-containing component is activated as a source feeding the pump current. The resulting pump current is detected as an index for the sought concentration of the specific oxygen-containing compound.

For the operation of the sensor in accordance with the invention, an evaluation circuit is required which makes available various electric voltages and which obtains the measurement signal from a current measurement.

Figure 2:
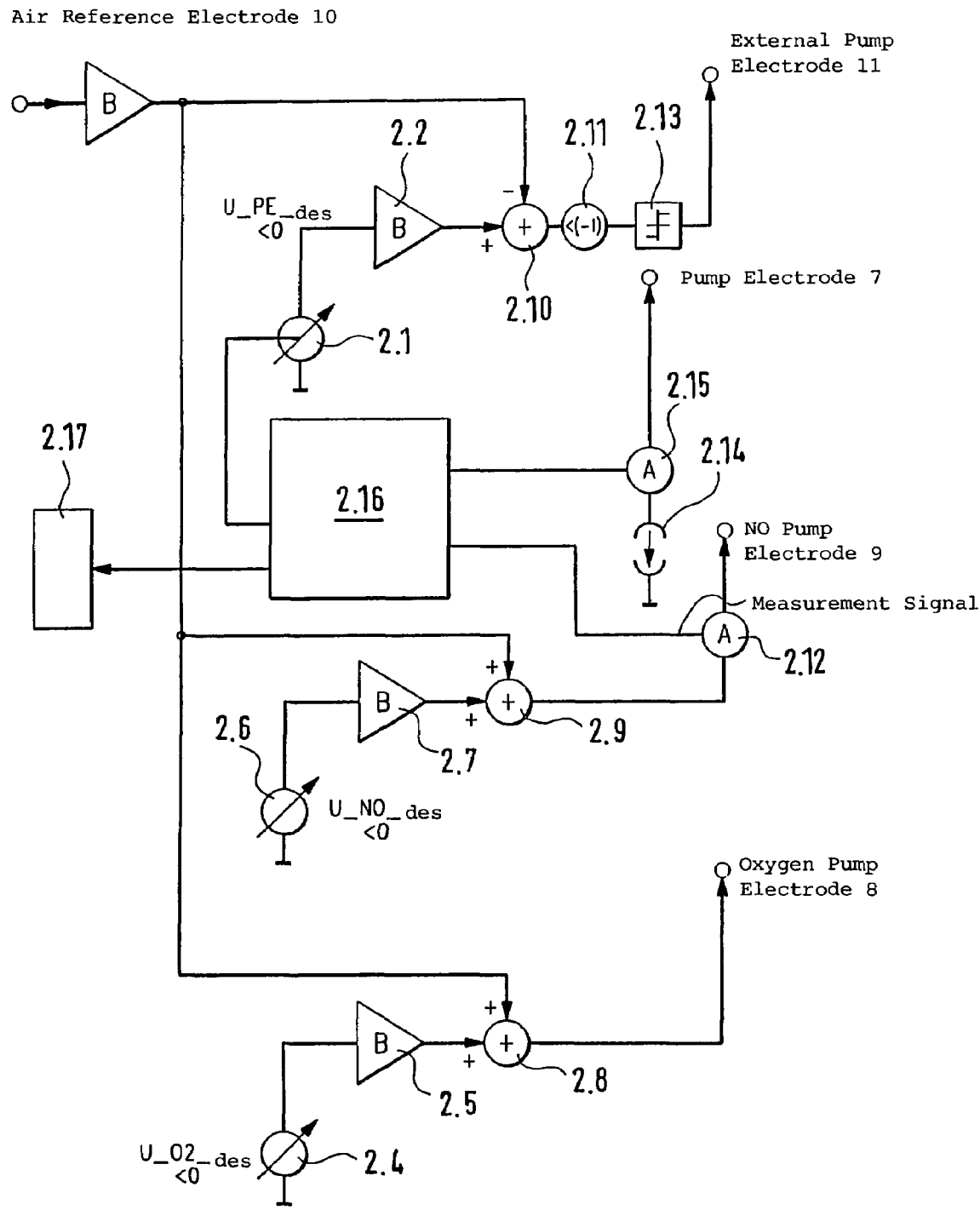
FIG. 2 shows a circuit for operating the sensor in accordance with the invention; and, FIG. 3 shows time-dependent traces of signals as they occur when carrying out the method of the invention.

The block circuit diagram of an evaluation circuit is shown in FIG. 2.

The oxygen pumping electrode 7 in the first cavity is, to a certain extent, at a virtual ground. This virtual ground is formed by a current source 2.14 which has a very low internal resistance. The current source 2.14 replaces the negative charge which flows off from the pump electrode 7 via the oxygen ion line through the solid electrode to the positive electrode 11. The pump current of the first chamber, which is detected by the current measuring apparatus 2.15, increases with increasing oxygen concentration in the external volume. The detected pump current can therefore be used as an index for the oxygen concentration and therewith, for example, for the control of the air/fuel ratio for the operation of a combustion process.

The counterelectrode 11 is raised to a potential which is positive relative to ground. This potential is shifted by the potential of the air reference electrode 10 via the logic connection 2.10. The inversion of the potential (U_IPE-des—potential of the air reference electrode), which is made available negative in block 2.11, causes, in the context of the embodiment shown, that the external oxygen pump electrode 11 is positive compared to the oxygen pump electrode 7.

The potential U_IPE_des is generated via a voltage reference 2.1 in combination with an operational amplifier 2.2 and is adjusted via a controller 2.13.

The voltages for the electrodes 8 and 9, which lie in the cavity 2, are generated via voltage references 2.4 and 2.6 and operational amplifiers 2.5 and 2.7. U_O2_des<0 is the voltage reference for the oxygen pump electrode 8 and U_NO_des<0 is the voltage reference for the NO pump electrode 9.

The potentials of electrodes 8 and 9 are also shifted by the logic circuits 2.8 and 2.9 by the potential of the air reference.

The other electrode potentials are determined directly. The NO pump current can be measured via known current voltage conversion. This function is represented by the current measuring apparatus 2.12.

Figure 3A:
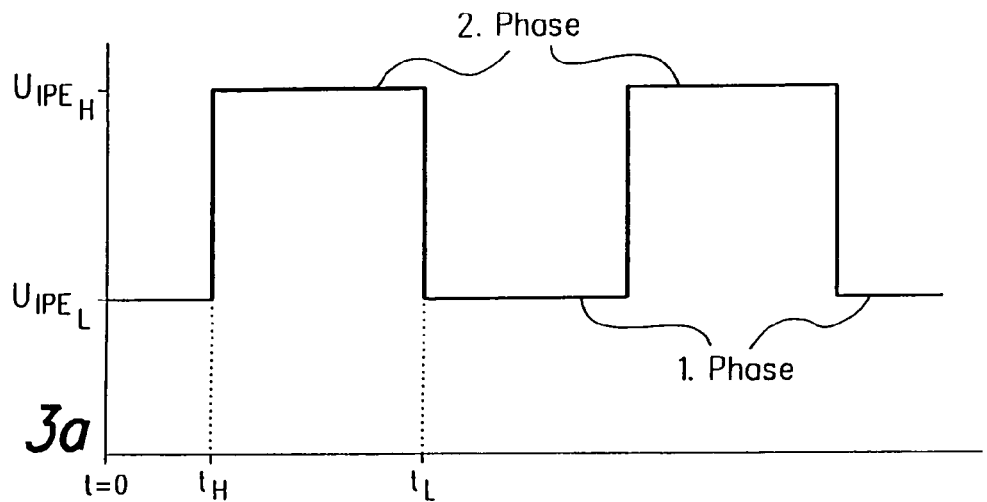
Figure 3B:
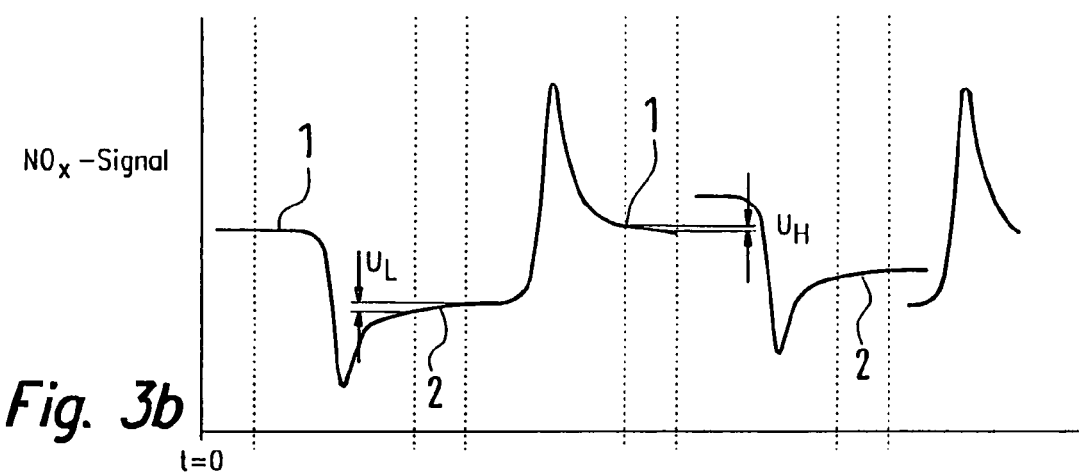

According to the invention, U_IPE-des is not approximately constant but is reversed back and forth in a pendular manner between two voltage values $U_{IPE\_H}$ and $U_{IPE\_L}$. The control takes place via a control chip 2.16 which has at least a processor and a program and data memory. A possible time-dependent trace of U_IPE-des is shown in FIG. 3a in a reversal to be viewed as an embodiment. FIG. 3b shows the corresponding trace of the pump current of the second cavity as it is detected by the current apparatus 2.12 and is transmitted to the control chip 2.16. According to one embodiment, this signal is identified in FIG. 3b as NOx signal. When this characterization is used in the following it is representative to a certain extent for any desired other oxygen-containing compounds which can be distinguished by the described multi-cavity principle from other oxygen-containing compounds.

The lower voltage $U_{IPE\_L}$ in FIG. 3a corresponds to the voltage which is known from the state of the art for the controlled state of the first oxygen pump electrode.

This voltage is characterized, inter alia, in that the oxygen concentration in the first chamber is, on the one hand, reduced but, on the other hand, a residual oxygen concentration is maintained for which a decomposition of NOx does not yet occur.

The nitrogen oxides therefore diffuse further into the second cavity and are there decomposed and bring about the NOx signal at the level 1 in FIG. 3b.

The oxygen pump electrodes of the first cavity can, at higher voltage, in addition to pumping oxygen from $O_2$, also pump oxygen from $H_2O$, CO and NO as well as from $NO_2$.

$U_{IPE\_H}$ is now selected so high that the pump electrode of the first cavity pumps, in addition to the oxygen of the exhaust gas, also the oxygen which is bonded in the nitrogen oxides, with $U_{IPE\_H}$ being, for example, 500 to 1000 mV especially, however, 600 to 850 mV.

The nitrogen oxide component in the first cavity then goes toward zero so that subsequently the resupply of nitrogen oxides from the first cavity to the second cavity does not occur.

Oxygen is pumped away from nitrogen oxides for the measurement also in the second cavity. For this reason, the nitrogen oxide concentration in the second cavity likewise drops to zero because of the absent resupply. After the nitrogen oxide concentration in the second cavity has reached steady state toward the value zero, the zero value of the signal can be determined. This is the level in FIG. 3b identified by 2.

Thereafter, the pump voltage, which acts in the first cavity, is reversed to the lower value $U_{IPE\_L}$.

After steady state of the signal is reached at the lower voltage, the signal value (level 1), which is burdened with the zero value, can be detected.

The subtraction of the signal value, which is burdened with the zero value, and the previous zero value in the control chip 2.16 yields the correct signal value which is to be outputted, with which, for example, the actuating quantities for the operation of an internal combustion engine are formed. This application of the NOx signal, which is formed in accordance with the invention, is represented by block 2.17.

A further embodiment discloses a possibility to greatly reduce pulse-shaped disturbances in the NOx signal which originate from high frequency interference.

This embodiment defines, to a certain extent, a validity test for the scanned signal values. It will be explained with respect to FIG. 3. Only the signal values will be viewed as valid which have no high rates of change of speed. In this way, especially the pulse-shaped reactions of the NOx signal to a level change of the pump voltage are suppressed.

Figure 3C:
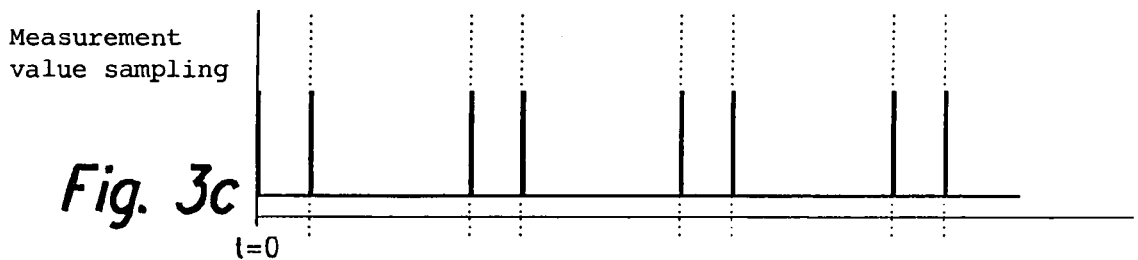
Figure 3D:
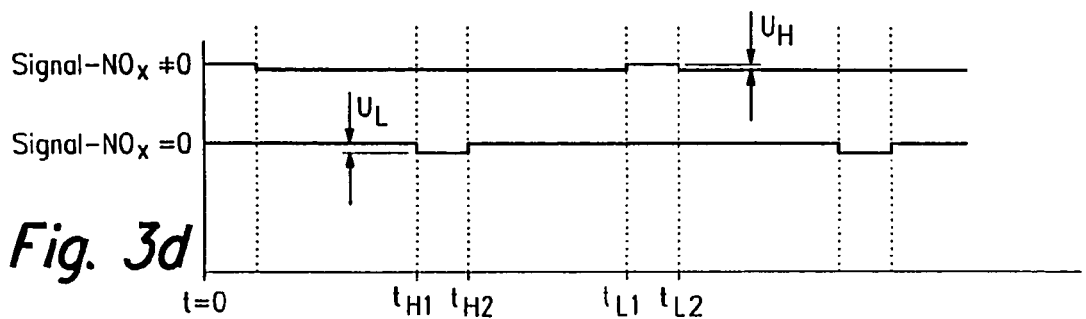

Assume that t=0 is the time point of the first change from $U_{IPE\_H}$ to $U_{IPE\_L}$ (see FIG. 3a). After the time $t_H$, the return switching from $U_{IPE\_L}$ to $U_{IPE\_H}$ takes place and after $t_L$ vice versa. After the time $t_{H1} > t_H$, a first sampling is taken from the nitrogen oxide signal of the evaluation circuit. The measurement value which is taken is represented in FIG. 3c by the pulses. Additional measurement values can be taken after $t_{H2}, t_{H3}, \ldots t_{Hn}$. With the taking of several samples, the difference of two sequential samples at time points $t_{Hi}$ and $t_{Hi+1}$ can be used as an index for evaluating the steady state performance. If the difference $U_H$, $U_L$ which is shown in FIG. 3d, is small enough, then the sample values are assumed to be valid. The upper line in FIG. 3d shows the scan-hold signal trace for the phases having lower pump voltage. This signal trace corresponds therefore to the NOx signal having a zero value. The lower line corresponds to the scan-hold signal trace for the phases having high pump voltage which supply the zero value of the NOx signal.

Signal disturbances, which are associated with abrupt changes, are greatly reduced by this validity test.

From the valid values, the final zero value can be formed by mean value formation.

The time span $t_H < t < t_L$ is treated in the same way except that one obtains, in lieu of the zero values, at the times $t_{Lm} > t_{Lm-1} \ldots > t_{L2} > t_{L1} > t_L$, the signal quantities shifted by the zero values.

The final signal value, which is burdened with the zero value, is formed also from the valid signal quantities via mean value formation.

The subtraction of signal value, which is burdened by zero value, and previous zero value yields the correct signal value to be outputted.

In addition to the mean value formation from the valid signal quantities (zero values), also other mathematical functions are conceivable which permit the generation of a final signal value (zero value), for example, weighted sums.

The invention is claimed is:

1. A method for determining the concentration of an oxygen-containing compound in a test gas in an external volume containing also additional oxygen, the method comprising the steps of:

providing a sensor arrangement including; a sensor having a first cavity connected to said external volume via a first diffusion barrier and a second cavity connected to the first cavity via a second diffusion barrier; means for reducing the oxygen concentration in said first cavity; and, means for detecting the concentration of oxygen in said second cavity;

reducing the oxygen concentration in said first cavity in a first phase to a value at which a change of the concentration of the oxygen-containing compound does not occur;

in a second phase in said first cavity, further reducing said oxygen concentration to a value at which also a reduction of the concentration of the first oxygen-containing compound takes place and forming an index for the sought concentration as a difference of the oxygen concentrations detected in said second cavity in said first and second phases; and, wherein the means for reducing the oxygen concentration in said first cavity includes a solid electrolyte which is arranged between two electrodes to which a voltage is applied; and, the voltage, which is supplied to said electrodes, is greater in the second phase than in the first phase.

2. The method of claim 1, wherein the means for detecting the concentration of oxygen in said second cavity includes a gas generating electrode for generating oxidizable gases.

3. The method of claim 1, wherein the means for detecting the concentration of oxygen in the second cavity contains two electrodes of which one electrode of said two electrodes facilitates the decomposition of oxygen and the other electrode of said two electrodes facilitates the decomposition of nitrogen oxides.

4. The method of claim 1, wherein the exhaust gas of a combustion process is said test gas.

5. The method of claim 1, wherein nitrogen oxides are the specific oxygen-containing compound the concentration of which is to be detected.

6. A method for determining the concentration of an oxygen-containing compound in a test gas in an external volume containing also additional oxygen, the method comprising the steps of:

providing a sensor arrangement including: a sensor having a first cavity connected to said external volume via a first diffusion barrier and a second cavity connected to the first cavity via a second diffusion barrier; means for reducing the oxygen concentration in said first cavity; and, means for detecting the concentration of oxygen in said second cavity;

reducing the oxygen concentration in said first cavity in a first phase to a value at which a change of the concentration of the oxygen-containing compound does not occur; and, in a second phase in said first cavity, further reducing said oxygen concentration to a value at which also a reduction of the concentration of the first oxygen-containing compound takes place and forming an index for the sought concentration as a difference of the oxygen concentrations detected in said second cavity in said first and second phases.

* * * * *

UNITED STATES PATENT AND TRADEMARK OFFICE
CERTIFICATE OF CORRECTION

| | |
|---|---|
| PATENT NO. | : 7,073,369 B2 |
| APPLICATION NO. | : 10/473357 |
| DATED | : July 11, 2006 |
| INVENTOR(S) | : Berndt Cramer and Bernd Schumann |

It is certified that error appears in the above-identified patent and that said Letters Patent is hereby corrected as shown below:

In column 7:
Line 1: Delete "including;" and substitute -- including: -- therefor.

Signed and Sealed this

Ninth Day of January, 2007

JON W. DUDAS
*Director of the United States Patent and Trademark Office*